United States Patent [19]

Wu

[11] 4,377,444
[45] Mar. 22, 1983

[54] RECOVERY AND PURIFICATION OF OLEFINIC NITRILES

[75] Inventor: Hsin C. Wu, Parma, Ohio

[73] Assignee: The Standard Oil Co., Cleveland, Ohio

[21] Appl. No.: 535,402

[22] Filed: Jan. 13, 1975

Related U.S. Application Data

[63] Continuation-in-part of Ser. No. 446,557, Feb. 27, 1979, abandoned, which is a continuation of Ser. No. 185,721, Oct. 1, 1971, abandoned, which is a continuation-in-part of Ser. No. 29,022, Apr. 16, 1970, abandoned.

[51] Int. Cl.$^3$ .............................................. B01D 3/34
[52] U.S. Cl. ............................ 203/96; 203/DIG. 3;
  203/DIG. 19; 260/465.3; 260/465.9
[58] Field of Search ...................... 203/84, 78, 85, 86,
  203/79, 76, 95–99, 42, DIG. 3, DIG. 19, 83;
  260/465.9, 465.3

[56] References Cited
U.S. PATENT DOCUMENTS

| | | | |
|---|---|---|---|
| 3,080,301 | 3/1963 | Fontana et al. | 203/97 |
| 3,196,085 | 7/1965 | Dippel | 203/97 |
| 3,264,197 | 8/1966 | Schonbeck et al. | 203/84 |
| 3,399,120 | 8/1968 | Lovett | 203/84 |
| 3,507,755 | 4/1970 | Bitners et al. | 203/96 |
| 3,535,849 | 10/1970 | Hausweiler et al. | 203/84 |

Primary Examiner—Frank Sever
Attorney, Agent, or Firm—John E. Miller, Jr.; Herbert D. Knudsen; Larry W. Evans

[57] ABSTRACT

A process is described for the recovery and purification of an olefinic nitrile, such as methacrylonitrile, from mixtures of said olefinic nitrile with hydrogen cyanide, acetonitrile, acrylonitrile, and carbonyl compounds, which result from the ammoxidation of an olefin, such as isobutylene. The mixtures of olefinic nitrile are fed to an extractive distillation column at a point above the middle of the column, a vapor sidestream is removed at a point below the middle of the extractive distillation column said sidestream containing substantially all of the hydrogen cyanide, acetonitrile and carbonyl compounds and then concentrating the hydrogen cyanide, acetonitrile and carbonyl compounds in a stripping pot.

6 Claims, 2 Drawing Figures

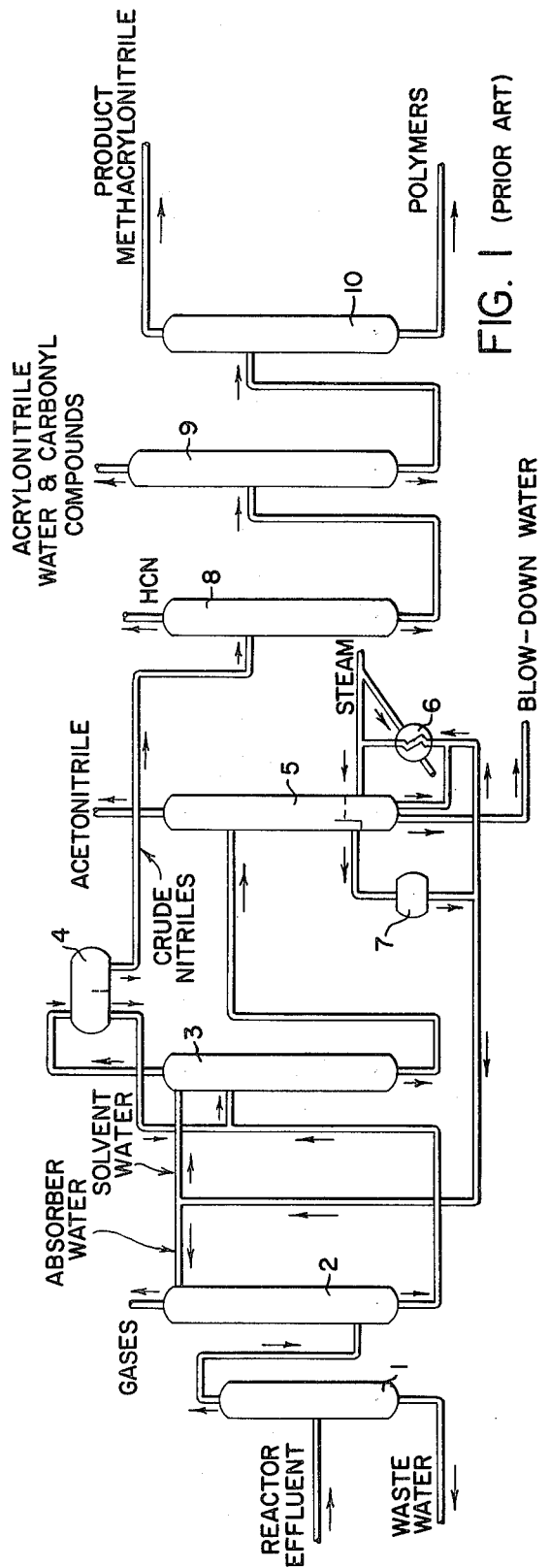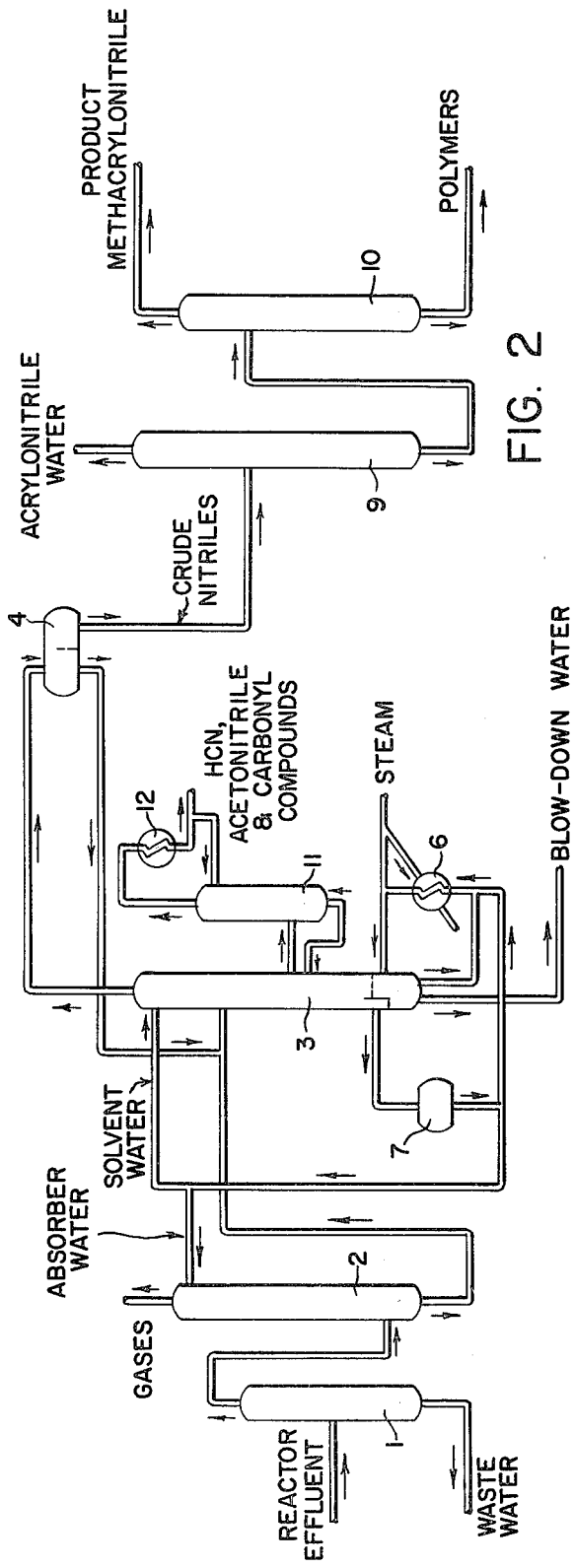

RECOVERY AND PURIFICATION OF OLEFINIC NITRILES

CROSS REFERENCE TO RELATED APPLICATIONS

This application is a continuation-in-part of my copending application Ser. No. 446,557 filed Feb. 27, 1974, now abandoned, which was a continuation of Ser. No. 185,721 filed Oct. 1, 1971, now abandoned, which was a continuation-in-part of Ser. No. 29,022 filed Apr. 16, 1970, now abandoned.

SUMMARY OF THE INVENTION

This invention relates to the recovery and purification of olefinic nitriles and more particularly pertains to an improved process for the recovery and purification of olefinic nitriles, such as methacrylonitrile and acrylonitrile, produced by the ammoxidation of isobutylene and propylene from mixtures of said olefinic nitriles with such materials as acetonitrile, hydrogen cyanide, propionitrile, butyronitrile, methacrolein, acrolein, acetone, acetaldehyde, etc.

Processes and catalysts for the production and recovery of methacrylonitrile and acrylonitrile are well known and have been disclosed in the patent literature, for instance, in U.S. Pat. Nos. 2,904,580; 3,149,055; 3,198,750; 3,230,246 and 3,352,764. When an olefin, such as isobutylene or propylene, is allowed to react with ammonia and molecular oxygen in the vapor phase at elevated temperatures and in the presence of an ammoxidation catalyst, the corresponding olefinic nitriles, such as methacrylonitrile and acrylonitrile, are produced along with varying amounts of by-products of the ammoxidation reaction including acetonitrile, hydrogen cyanide, propionitrile, butyronitrile, methacrolein, acrolein, acetone, acetaldehyde, and mixtures of the desired olefinic nitrile, and some of these by-products appear in the ammoxidation reactor effluent. Usually, the products of the ammoxidation reaction are recovered in a first step by absorption in water during which step some heavy or high-boiling organic compounds are formed through polymerization, condensation, etc., of some of the lighter organic products. It is an object of this invention to provide an improved method for separating the olefinic nitriles from the by-products formed in the ammoxidation reaction as well as from the heavy organic compounds.

Although the process of the present invention is applicable to the recovery and purification of either methacrylonitrile or acrylonitrile as well as mixtures of the two, the following description will be illustrated in terms of methacrylonitrile recovery and purification for simplicity of description, as well as because the process of this invention is most advantageous when applied to the recovery and purification of methacrylonitrile.

The present invention can be better understood when reference is made to the accompanying drawing wherein:

FIG. 1 is a flow diagram illustrating the recovery and purification of methacrylonitrile by a conventional scheme.

FIG. 2 is a flow diagram illustrating a specific embodiment of the improved process for the recovery and purification of methacrylonitrile according to the present invention.

In U.S. Pat. No. 3,198,750, a catalyst is described for the manufacture of methacrylonitrile by the gaseous phase catalytic reaction of isobutylene, ammonia, and a molecular oxygen-containing gas. In this vapor phase catalytic reaction which can be carried out in a fixed bed or fluidized bed type of reactor, a part of the ammonia which is introduced as feed to the reactor does not react and consequently appears in the reactor effluent along with methacrylonitrile, oxygen, nitrogen, and the aforementioned by-products.

In one recovery and purification scheme illustrated in FIG. 1, the reactor effluent, after briefly heat exchanging with the incoming feed gases, is led to the bottom of a quench tower 1 in which it is countercurrently scrubbed with diluted sulfuric acid. Other mineral acids, such as phosphoric, nitric, and hydrochloric acids, may also be used. The acid reacts with ammonia forming a salt and thus neutralizing the ammonia and making the ammonia unavailable for the formation of by-products resulting from the direct reaction of ammonia with methacrylonitrile, acrylonitrile, or other products of the reaction. Despite the speed of the neutralization reaction in the quench tower 1, some side reactions do occur as not all of the excess ammonia in the reactor effluent can be neutralized fast enough to prevent some reaction between the ammonia and other components of the reactor effluent. As a result, some higher condensation products and polymers are formed at this point, some of which are quite heavy and most of which are characteristically soluble in water. Consequently, the stream issuing from the bottom of the quench tower 1 is a diluted water solution of the ammonium salt of the mineral acid used, methacrylonitrile, acrylonitrile, hydrogen cyanide, and other by-products of the reaction as well as higher boiling condensation products and organic polymers.

In a subsequent step, the overhead from the quench tower 1 is led into an absorber 2 where it is countercurrently contacted with descending water solvent, into which the products of reaction, except for relatively insoluble gases, are absorbed. The non-absorbed gases are vented and disposed of. The stream from the bottom of absorber 2, known as the rich water stream, is led to an extractive distillation column having multiple distillation trays, which is hereinafter referred to as a recovery column 3, where it is extractively distilled. The recovery column 3 may be any suitable contacting means in which liquid and vapor are countercurrently contacted in a multiplicity of inter-communicating zones or stages. The overhead vapors from the recovery column 3 are enriched in methacrylonitrile and acrylonitrile, other components being chiefly water and hydrogen cyanide. When these overhead vapors are condensed and collected in the decanter 4, the condensed liquid undergoes liquid-liquid phase separation resulting in an organic phase (upper layer) and an aqueous phase (lower layer). The organic phase (crude nitriles) is composed primarily of methacrylonitrile saturated with water and contaminated with acrylonitrile, hydrogen cyanide, and carbonyl compounds. The lower aqueous phase from the decanter 4, which is composed of water saturated with methacrylonitrile and contaminated with hydrogen cyanide, is recycled to the feed of the recovery column 3. The liquid bottoms from the recovery column 3, depleted in methacrylonitrile and acrylonitrile, are pumped to the stripper column 5. A thermosiphon reboiler 6, in cooperation with a large quantity of live steam injected into the bottom of a stripper column 5 provides the required heat duty or "boil up" in the bottom of the stripper column 5. The acetonitrile vapors, contaminated chiefly with hydrogen cyanide and saturated with water, are condensed, a portion of which being withdrawn and the remaining portion being returned to the top of the stripper column 5. The liquid bottoms stream from the bottom of the stripper column 5 is mainly water contaminated with organic "heavies" and various cyanides. A small portion of this stream is withdrawn to waste treatment, the remainder being returned to the absorber 2 as lean water and to the top of recovery column 3 as solvent water, which is necessary for washing the acetonitrile down to the bottoms in the extractive distillation. When it is desired to reduce the volume of the stripper column 5 blowdown water, it has been the practice that the stripper bottoms stream is totally withdrawn to a surge tank 7 from the bottom tray of the stripper column 5. From the surge tank 7, the amount of water required to meet the absorber lean water and the recovery solvent water requirements is withdrawn. The remainder is sent to the thermosiphon reboiler 6 section for partial vaporization and thus achieving volume reduction. The partially vaporized water, containing a higher level of organic heavies as a result of volume reduction, is then sent to waste treatment.

The crude nitriles from the top of decanter 4 are led to a hydrogen cyanide column 8 for separation of hydrogen cyanide from the bulk of the methacrylonitrile. The overhead from the hydrogen cyanide column 8, containing chiefly hydrogen cyanide and very small amounts of carbonyl compounds, is condensed and collected. A portion of this condensate is withdrawn to waste treatment or by-product recovery. The remainder is sent to the top of the column as reflux. The bottoms stream of hydrogen cyanide column 8, chiefly methacrylonitrile with small amounts of acrylonitrile, water, carbonyl compounds, and cyanohydrins, is led to an acrylonitrile column 9, in which acrylonitrile, water, and carbonyl compounds are concentrated in the upper section. The overhead vapor from the acrylonitrile column 9 is condensed and collected and a portion is sent to waste treatment or acrylonitrile recovery, and the remainder is sent to the top of the acrylonitrile column 9 as reflux. The bottoms stream of acrylonitrile column 9, primarily methacrylonitrile with very small amounts of polymers and cyanohydrins, is led to product column 10, where the product methacrylonitrile is withdrawn at the top and the polymers and cyanohydrins are concentrated in the lower section of the column and withdrawn at the bottom and sent to waste treatment. The bottoms stream containing some methacrylonitrile may be further processed to recover the residual methacrylonitrile. This can be done by either distillation, vacuum flashing operation, or recycling back to the recovery column 3 feed.

FIG. 2 is a flow diagram which illustrates a specific embodiment of the process of the present invention. In FIG. 2, as in FIG. 1, the reactor effluent, after briefly heat exchanging with incoming ammoxidation reactor feed gases, is led to the bottom of a quench tower 1 in which it is countercurrently scrubbed with dilute acid. The stream issuing from the bottom of the quench tower 1 is waste water. The overhead from quench tower 1 is led into an absorber 2 where it is countercurrently contacted with descending water solvent. The rich water stream from the bottom of absorber 2 is led to recovery column 3 and the non-absorbed gases are vented. The process of the present invention illustrated in FIG. 2 differs in several respects from that shown in FIG. 1. In the process of this invention a vapor sidestream which is rich in hydrogen cyanide, acetonitrile, and carbonyl compounds is withdrawn from near the bottom section of the recovery column 3 and the sidestream passes into a stripping pot 11 when hydrogen cyanide, acetonitrile, and carbonyl compounds are separated from the crude nitriles. It has been found that the process of this invention is extremely effective and economical in that it not only saves a substantial amount of the capital investment required to build a commercial production unit but also improves the product purity of the final methacrylonitrile product. Further advantages of the instant process are lower utilities (steam, electrical power, and cooling water) consumption, lower plant maintenance requirement, and higher efficiency of methacrylonitrile monomer recovery.

In FIG. 2 the recovery column 3 has a total of 85 fractionating trays. In FIG. 2 the feed stream (rich water) is fed to tray No. 55 from the bottom of the recovery column 3. Other liquid-vapor contacting means such as columns packed with Raschig rings, Berl saddles, and the like may be used, but sieve trays or valve trays are preferred in the recovery column 3. The vapors distilled overhead from the recovery column 3 are condensed in a conventional condenser (not shown) and the condensate then passes to the decanter 4 where a phase separation takes place, the organic phase (upper layer) being removed and fed to the acrylonitrile column 9 for further purification and the water phase (lower layer) being recycled to the feed of the recovery column 3. A vapor sidestream drawoff is withdrawn from tray No. 25 from the bottom of the recovery column 3 and passes into an organic stripping pot 11 to enrich the hydrogen cyanide, acetonitrile, and carbonyl compounds (such as methacrolein, acrolein, acetone, acetaldehyde, etc.) in the uppersection. The overhead vapor from the organic stripping pot 11 is condensed in a condenser 12 and most of the condensate is returned to the top tray of the organic stripping pot 11 by gravity flow. A small stream of the condensate is withdrawn and sent to waste treatment or by-product recovery. This overhead drawoff can also be drawn as vapor by partially condensing the overhead vapor of the organic stripping pot 11 in the condenser 12. The organic stripping pot 11 is fitted with 20 fractionating trays. It will be apparent to one skilled in the art that the organics can be further concentrated by installing more trays in the stripping pot 11. Also, other liquid-vapor contacting means such as columns packed with Raschig rings, Berl saddles, and the like may be used here, but sieve trays or valve trays are preferred. The liquid bottoms of the organic stripping pot 11 is fed back to the recovery column 3 at the same tray (tray No. 25) where the vapor sidestream is drawn off. The liquid flow is by gravity. A pump, of course, can be used but it is not necessary.

The recovery column 3 may be reboiled by heat exchange with any hot fluid. Condensing steam as the transfer medium in the thermosiphon reboiler is a preferred method of reboiling the recovery column 3. In addition, live steam may be injected directly into the recovery column 3 either to supplement or to replace the heat duty provided by the reboilers. The downflowing liquid in the recovery column 3 is totally withdrawn from the bottom tray (tray No. 1) into a surge tank 7 from which an amount of water, equivalent to the combined requirement of the absorber water and recovery column 3 solvent water, is withdrawn and recycled to the absorber 2 and the recovery column 3. The remainder is pumped to the section of the recovery column reboiler 6 for volume reduction through partial vaporization by the condensing steam in the reboiler 6. After the volume reduction, the remaining water containing a higher level of heavies is then sent to waste treatment. This water stream is designated as the blowdown water. It is clear that in the process of the present invention the use of the stripper column 5 illustrated in FIG. 1 is eliminated. Also in the process of this invention the crude nitriles from the decanter 4 are passed directly to the acrylonitrile column 9. The hydrogen cyanide column 8, illustrated in FIG. 1 for separating the hydrogen cyanide from the bulk of the methacrylonitrile, is not necessary in the instant process. The use of the organic stripping pot 11, which is much smaller in size as compared to the stripper column 5 and the hydrogen cyanide column 8, has accomplished the separation of hydrogen cyanide and acetonitrile from methacrylonitrile in the instant process. The sidestream vapor drawoff technique of this invention also reduces the carbonyl compounds, particularly methacrolein, in the crude nitriles and, as a result, a purer final methacrylonitrile product is produced. The composition comparison of the various streams including the crude nitriles and the final product produced by the conventional scheme of FIG. 1 and by the process of this invention is presented in Table I.

dissolved methacrolein will also recycle and contaminate the recovered methacrylonitrile. In the instant process virtually all of the methacrolein is separated from the crude nitriles. This makes it possible to recover the dissolved methacrylonitrile. A small distillation column, preferably fitted with a total of 10 dual-flow trays, will be needed to strip most of the dissolved organics. The stripped waste water will be easier to dispose of as it contains a lower level of organics.

It is apparent to one skilled in the art that the number of trays in the recovery column 3 can be varied by 85±30 distillation trays and the column can still be used as described above. The preferred 85-tray recovery column 3 will operate as described even if the feed tray and the sidestream vapor drawoff tray were relocated upwards or downwards by as many as 20 trays, but there would be no special reason or advantage for doing this. Furthermore, the recovery solvent water temperature and rate have a marked effect on the column performance. The more solvent water that is used, the lower the concentrations of hydrogen cyanide, acetonitrile, and carbonyl compounds will be in the crude nitriles. It has also been observed that when the solvent water temperature is lowered the crude nitriles are cleaner. The recovery column 3 temperature profile is another important variable. Normally, in a 85-tray recovery column 3, the temperature control is located at about tray No. 40. If this temperature is too high, exces-

TABLE I

| Composition of Streams (Weight Percent) | Waste Water From Quench Tower 1 | Crude Nitriles From Decanter 4 By FIG. 1 Process | Crude Nitriles From Decanter 4 By FIG. 2 Process | FIG. 2 Process Organic Stripping Pot 11 Overhead | Final Product By FIG. 1 Process | Final Product By FIG. 2 Process |
|---|---|---|---|---|---|---|
| Methacrylonitrile | 0.55 | 79.389 | 92.9 | — | 99.615 | 99.645 |
| Acrylonitrile | 0.04 | 3.5 | 4.0 | — | 0.05 | 0.05 |
| Acetonitrile | 0.2 | 0.006 | 0.001 | 4.5 | 0.002 | 0.0005 |
| Hydrogen Cyanide | 0.34 | 12.0 | 0.05 | 40.0 | 0.002 | 0.0005 |
| Propionitrile | — | 0.008 | 0.002 | — | 0.004 | 0.001 |
| Butyronitrile | — | 0.02 | 0.01 | — | — | — |
| Isobutyronitrile | — | 0.05 | 0.02 | 0.2 | 0.003 | 0.001 |
| Acrolein | — | 0.005 | 0.001 | — | — | — |
| Methacrolein | 0.2 | 0.3 | 0.01 | 4.0 | 0.02 | 0.001 |
| Acetone | — | 0.02 | 0.005 | 0.5 | 0.004 | 0.001 |
| Acetaldehyde | — | 0.002 | 0.001 | — | — | — |
| Water | 85.17 | 4.7 | 3.0 | 50.8 | 0.3 | 0.3 |
| Organic Polymers | 1.0 | — | — | — | — | — |
| Cyanohydrins | 0.5 | — | — | — | — | — |
| Ammonium Sulfate | 12.0 | — | — | — | — | — |

It can be seen in Table I that the methacrolein contamination in the methacrylonitrile product produced by the present process is relatively low. The methacrylonitrile produced by the process of this invention also contains much less hydrogen cyanide than that produced heretofore. The hydrogen cyanide present in the methacrylonitrile product is probably produced by the breakdown of cyanohydrins which are the products of the reversible reaction between hydrogen cyanide and carbonyl compounds. The crude nitriles of the present invention contain extremely low hydrogen cyanide and carbonyl compound contamination as shown in Table I; consequently, the concentration of cyanohydrins is also very low. This results in a much lower level of hydrogen cyanide contamination in the final methacrylonitrile product.

As illustrated in Table I, the quench tower 1 waste water contains some methacrylonitrile. In the process illustrated in FIG. 1, it has not been practical to try to recover this dissolved methacrylonitrile because the sive amounts of hydrogen cyanide, acetonitrile, and carbonyl compounds will go up to the overheaad crude nitriles. If this temperature is too low, a significant amount of methacrylonitrile may be lost in the sidestream drawoff vapor and eventually in the crude hydrogen cyanide stream.

It has been found that the control temperature at about tray No. 40 is best maintained at 190° F. to 200° F., with the solvent water temperature in the range of 60° F. to 120° F. and a solvent water-to-methacrylonitrile monomer in the recovery column 3 feed weight ratio of 5:1 to 30:1. When the solvent water is maintained in the range of from 140° F. to 190° F. as in U.S. Pat. No. 3,399,120 the organic material going to the decanter 4 contains from about 10 to 12% by weight of HCN and about 0.5% by weight of methacrolein. When, according to the instant process the solvent water is maintained in the range of 60° F. to 120° F. the organic material going to decanter 4 contains about 0.03% by weight of HCN and about 0.01% by weight of methacrolein. The pressure in the top of the recovery column 3 is about 1–5 psig and the temperature about 170° F. to 180° F., and the pressure in the bottom is about 7–11 psig and the temperature about 230° F. to 250° F. The recovery column 3 in the conventional operation is generally run at a higher temperature profile, a higher solvent water temperature, and at about the same solvent water ratio to distill the hydrogen cyanide into the crude nitriles. In the conventional process a significant amount of carbonyl compounds is also included in the overhead crude nitriles.

As a further method of distinguishing over Lovett and U.S. Pat. No. 3,399,120 in the recovery and purification of acrylonitrile, it has been found by means of a computer simulation that using a solvent water temperature of 120° F. as compared to a solvent water temperature of 140° F. as shown by Lovett results in an improved bottoms effluent. The bottoms effluent from the extractive distillation of the invention using solvent water temperature of 120° F. is very much purer than the extractive distillation of the art. These results are summarized in the following table:

TABLE II

EFFECT OF SOLVENT WATER TEMPERATURE ON BOTTOMS STREAM FROM EXTRACTIVE DISTILLATION COLUMN
Bottoms Stream, Lbs./Hr.

| Component | Art Solvent Water, 140° F. | Invention Solvent Water, 120° F. |
|---|---|---|
| Acrylonitrile | 0 | 0 |
| Acetonitrile | 2.247 | 0.00289 |
| HCN | 0.00048 | 0.00029 |
| Water | 337,875 | 350,511 |

We claim:

1. In the process for the recovery of an olefinic nitrile from a mixture of said olefinic nitrile and other olefinic nitriles, hydrogen cyanide, acetonitrile, and carbonyl compounds, said mixture being produced by the ammoxidation of an olefin, the improvement comprising
   (a) feeding to an extractive distillation column equipped with several fractionating trays at a point above the middle of the extractive distillation column a mixture of the olefinic nitrile, hydrogen cyanide, acetonitrile, and carbonyl compounds,
   (b) feeding solvent water to the extractive distillation column at a temperature in the range of 60° F. to 120° F., and
   (c) removing a vapor sidestream at a point below the middle of the extractive distillation column, and removing from said sidestream substantially all of the hydrogen cyanide, acetonitrile and carbonyl compounds.

2. The process of claim 1 wherein the olefinic nitrile is selected from the group consisting of acrylonitrile and methacrylonitrile and the olefin is a member selected from the group consisting of propylene and isobutylene.

3. The process of claim 2 wherein the extractive distillation column contains 85±30 distillation trays.

4. The process of claim 3 wherein a temperature is maintained in the range of 170° F. to 180° F. and a pressure is maintained in the range of 1–5 psig at the top of the extractive distillation column and a temperature is maintained in the range of 230° F. to 250° F. and a pressure is maintained in the range of 7–11 psig in the bottom of the extractive distillation column.

5. The process of claim 1 wherein the olefinic nitrile is methacrylonitrile.

6. The process of claim 1 wherein the olefinic nitrile is acrylonitrile.

* * * * *